US012109432B2

(12) United States Patent
Vayser et al.

(10) Patent No.: US 12,109,432 B2
(45) Date of Patent: *Oct. 8, 2024

(54) FIDUCIAL MARKER FOR ONCOLOGICAL AND OTHER PROCEDURES

(71) Applicant: Videra Surgical Inc., San Francisco, CA (US)

(72) Inventors: Alex Vayser, Mission Viejo, CA (US); Sunny Mitchell, Westport, CT (US); Henry Jay Lee, Chappaqua, NY (US); Joseph Guido, San Francisco, CA (US)

(73) Assignee: Videra Surgical Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/355,984

(22) Filed: Jul. 20, 2023

(65) Prior Publication Data

US 2023/0364444 A1 Nov. 16, 2023

Related U.S. Application Data

(63) Continuation of application No. 18/166,393, filed on Feb. 8, 2023, now Pat. No. 11,819,709, which is a
(Continued)

(51) Int. Cl.
*A61N 5/10* (2006.01)
*A61B 90/00* (2016.01)
(Continued)

(52) U.S. Cl.
CPC .......... *A61N 5/1007* (2013.01); *A61N 5/1049* (2013.01); *G06T 7/0012* (2013.01);
(Continued)

(58) Field of Classification Search
CPC .......... A61N 5/1007; A61N 2005/1008; A61N 2005/1062; A61N 5/1049;
(Continued)

(56) References Cited

U.S. PATENT DOCUMENTS 5,610,967 A 3/1997 Moorman et al.
6,174,330 B1 1/2001 Stinson
(Continued)

FOREIGN PATENT DOCUMENTS

EP 0894503 A2 2/1999
WO WO-2007045913 A2 4/2007
(Continued)

OTHER PUBLICATIONS

"U.S. Appl. No. 16/160,229, Final Office Action mailed Jun. 15, 2021", 13 pgs.
(Continued)

*Primary Examiner* — Siamak Harandi
(74) *Attorney, Agent, or Firm* — Schwegman Lundberg & Woessner, P.A.

(57) ABSTRACT

A method and apparatus for marking a target with a radiopaque marker is disclosed. The method may include providing a radiopaque filament and inserting at least portion of the radiopaque filament into tissue. The filament may extend continuously and at last partially around a perimeter of the target so that the filament is disposed in a plurality of surgical planes to demarcate the target with the radiopaque maker.

31 Claims, 10 Drawing Sheets

Related U.S. Application Data continuation of application No. 17/817,115, filed on Aug. 3, 2022, now Pat. No. 11,602,642, which is a continuation of application No. 16/791,410, filed on Feb. 14, 2020, now Pat. No. 11,464,998.

(60) Provisional application No. 62/943,464, filed on Dec. 4, 2019, provisional application No. 62/805,595, filed on Feb. 14, 2019.

(51) Int. Cl.
*G06T 7/00* (2017.01)
*A61B 17/00* (2006.01)

(52) U.S. Cl.
CPC ............... *A61B 2017/00004* (2013.01); *A61B 2090/3908* (2016.02); *A61B 2090/3966* (2016.02); *A61B 2090/3991* (2016.02); *A61N 2005/1008* (2013.01); *A61N 2005/1058* (2013.01); *A61N 2005/1062* (2013.01); *G06T 2207/10081* (2013.01); *G06T 2207/30068* (2013.01); *G06T 2207/30096* (2013.01); *G06T 2207/30204* (2013.01)

(58) Field of Classification Search
CPC .......... A61N 2005/1058; G06T 7/0012; G06T 2207/10081; G06T 2207/30068; G06T 2207/30096; G06T 2207/30204; A61B 2090/3966; A61B 90/39; A61B 2090/3908; A61B 2090/3991; A61B 2017/00004
See application file for complete search history.

(56) References Cited

U.S. PATENT DOCUMENTS

| | | | |
|---|---|---|---|
| 6,436,026 | B1 | 8/2002 | Sioshansi et al. |
| 7,083,641 | B2 | 8/2006 | Stinson et al. |
| 9,199,092 | B2 | 12/2015 | Stubbs et al. |
| 11,464,998 | B2 | 10/2022 | Vayser et al. |
| 11,602,642 | B2 | 3/2023 | Vayser et al. |
| 2002/0082683 | A1 | 6/2002 | Stinson et al. |
| 2004/0116802 | A1 | 6/2004 | Jessop et al. |
| 2004/0242953 | A1 | 12/2004 | Good |
| 2005/0020916 | A1 | 1/2005 | MacFarlane et al. |
| 2006/0079770 | A1 | 4/2006 | Sirimanne et al. |
| 2006/0116713 | A1 | 6/2006 | Sepetka et al. |
| 2007/0276494 | A1 | 11/2007 | Ferree |
| 2007/0288082 | A1 | 12/2007 | Williams |
| 2008/0021313 | A1 | 1/2008 | Eidenschink et al. |
| 2010/0222672 | A1 | 9/2010 | Macfarlane et al. |
| 2011/0125253 | A1 | 5/2011 | Casanova et al. |
| 2012/0330153 | A1 | 12/2012 | Sirimanni et al. |
| 2013/0178948 | A1 | 7/2013 | Tseng et al. |
| 2013/0180966 | A1 | 7/2013 | Gross et al. |
| 2013/0184577 | A1 | 7/2013 | Corbitt, Jr. et al. |
| 2014/0180065 | A1 | 6/2014 | Garcia |
| 2014/0257378 | A1 | 9/2014 | Norton et al. |
| 2015/0148837 | A1 | 5/2015 | Shinar et al. |
| 2015/0297316 | A1* | 10/2015 | Grinstaff ............... A61B 90/39 600/431 |
| 2015/0327861 | A1 | 11/2015 | Jackson et al. |
| 2018/0085184 | A1 | 3/2018 | Bolan et al. |
| 2018/0263706 | A1 | 9/2018 | Averbuch |
| 2018/0344429 | A1 | 12/2018 | Stewart |
| 2019/0110859 | A1* | 4/2019 | Baker .................... A61B 90/39 |
| 2020/0261742 | A1 | 8/2020 | Vayser et al. |
| 2023/0010957 | A1 | 1/2023 | Vayser et al. |
| 2023/0134658 | A1 | 5/2023 | Vayser et al. |
| 2023/0218924 | A1 | 7/2023 | Vayser et al. |
| 2024/0058623 | A1 | 2/2024 | Vayser et al. |

FOREIGN PATENT DOCUMENTS

| | | |
|---|---|---|
| WO | WO-2018097891 A1 | 5/2018 |
| WO | WO-2020168181 A1 | 8/2020 |
| WO | WO-2023070084 A1 | 4/2023 |

OTHER PUBLICATIONS

"U.S. Appl. No. 16/160,229, Non Final Office Action mailed Dec. 28, 2020", 13 pgs.

"U.S. Appl. No. 16/160,229, Non Final Office Action mailed Dec. 29, 2021", 22 pgs.

"U.S. Appl. No. 16/160,229, Notice of Allowance mailed May 9, 2022", 10 pgs.

"U.S. Appl. No. 16/160,229, Response filed Mar. 23, 2022 to Non Final Office Action mailed Dec. 29, 2021", 11 pgs.

"U.S. Appl. No. 16/160,229, Response filed Apr. 28, 2021 to Non Final Office Action mailed Dec. 28, 2020", 14 pgs.

"U.S. Appl. No. 16/160,229, Response filed Nov. 12, 2021 to Final Office Action mailed Jun. 15, 2021", 15 pgs.

"U.S. Appl. No. 16/791,410, Corrected Notice of Allowability mailed Sep. 14, 2022", 3 pgs.

"U.S. Appl. No. 16/791,410, Examiner Interview Summary mailed Jul. 25, 2022", 3 pgs.

"U.S. Appl. No. 16/791,410, Non Final Office Action mailed May 27, 2022", 18 pgs.

"U.S. Appl. No. 16/791,410, Notice of Allowance mailed Jul. 29, 2022", 8 pgs.

"U.S. Appl. No. 16/791,410, Response filed Jul. 18, 2022 to Non Final Office Action mailed May 27, 2022", 12 pgs.

"U.S. Appl. No. 17/817, 115, Notice of Allowance mailed Feb. 2, 2023", 11 pgs.

"U.S. Appl. No. 17/817, 115, Preliminary Amendment Filed Oct. 3, 2022", 7 pgs.

"U.S. Appl. No. 18/166,393, Non Final Office Action mailed Jun. 16, 2023", 15 pgs.

"U.S. Appl. No. 18/166,393, Notice of Allowance mailed Jul. 6, 2023", 8 pgs.

"U.S. Appl. No. 18/166,393, Preliminary Amendment Mar. 20, 2023", 6 pgs.

"U.S. Appl. No. 18/166,393, Response filed Jun. 22, 2023 to Non Final Office Action mailed Jun. 16, 2023", 9 pgs.

"Core Needle Biopsy of the Breast", American Cancer Society, [Online] Retrieved from the Internet: <URL: https://web.archive.org/web/20190508015215/https://www.cancer.org/cancer/breast-cancer/screening-tests-and-early-detection/breast-biopsy/core-needle-biopsy-of-the-breast.html>, (Oct. 9, 2017), 5 pgs.

"European Application Serial No. 20754954.4, Communication Pursuant to Rules 161(2) and 162 EPC mailed Oct. 1, 2021", 8 pgs.

"European Application Serial No. 20754954.4, Extended European Search Report mailed Oct. 19, 2022", 4 pgs.

"European Application Serial No. 20754954.4, Response filed May 18, 2023 to Extended European Search Report mailed Oct. 19, 2022", 8 pgs.

"International Application Serial No. PCT/US2020/018276, International Preliminary Report on Patentability mailed Aug. 26, 2021", 9 pgs.

"International Application Serial No. PCT/US2020/018276, International Search Report mailed Apr. 28, 2020", 2 pgs.

"International Application Serial No. PCT/US2020/018276, Written Opinion mailed Apr. 28, 2020", 7 pgs.

"International Application Serial No. PCT/US2022/078503, International Search Report mailed Mar. 14, 2023", 4 pgs.

"International Application Serial No. PCT/US2022/078503, Invitation to Pay Additional Fees mailed Jan. 3, 2023", 2 pgs.

"International Application Serial No. PCT/US2022/078503, Written Opinion mailed Mar. 14, 2023", 6 pgs.

"Surgical Suturing Techniques Mastery Guide", The Apprentice Doctor, [Online] Retrieved from the Internet: <URL: https://www.theapprenticedoctor.com/complete-guide-to-mastering- suturing-techniques/>, (Mar. 11, 2015), 21 pgs.

(56) References Cited

OTHER PUBLICATIONS

Ingle, Nilesh P, et al., "Mechanical Performance and Finite Element Analysis of Bi-directional Barbed Sutures", North Carolina State University, (Aug. 2003), 1-126.

Jin-Cheol, Kim, et al., "Comparison of tensile and knot security properties of saurgical sutures", Mater Sci: Mater Med, 18, (Year: 2007), (Jun. 14, 2007), 2363-2369.

Shah, Stuti R, et al., "Effect of Barium Sulphate As A Filler In Thermoplastic Polymer For Medical Applications", Medical Plastics Data Service, [Online] Retrieved from the Internet: <URL: http://www.medicalplasticsindia.com/mpds/2014/jan/coverstory5.htm>, (Jan. 2014), 3 pgs.

"International Application Serial No. PCT/US2022/078503, International Preliminary Report on Patentability mailed May 2, 2024", 8 pgs.

"International Application Serial No. PCT/US2024/025825, Invitation to Pay Additional Fees mailed Jul. 19, 2024", 2 pgs.

\* cited by examiner

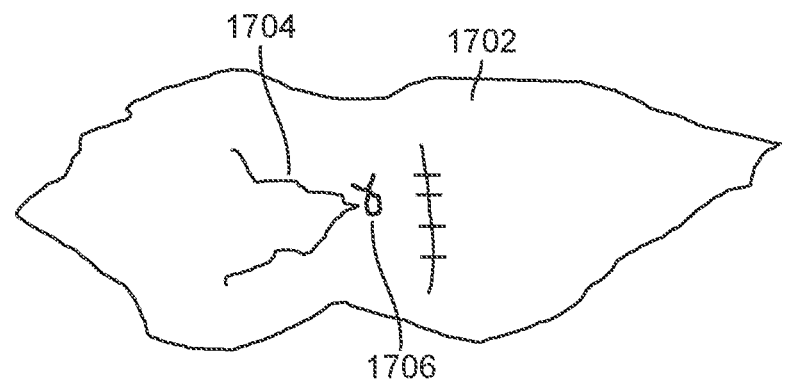
FIG. 17
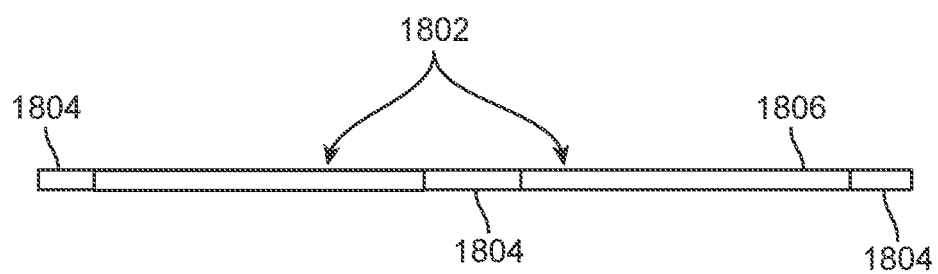
FIG. 18
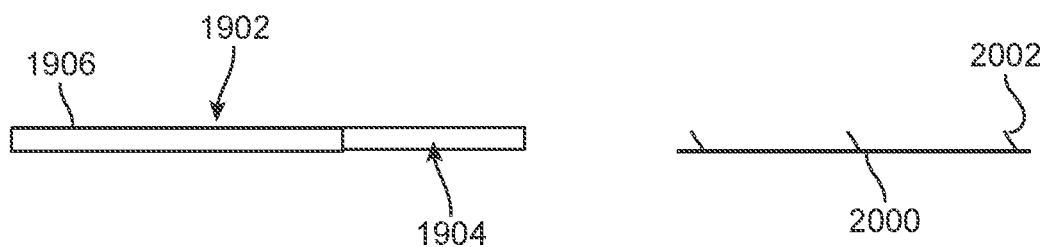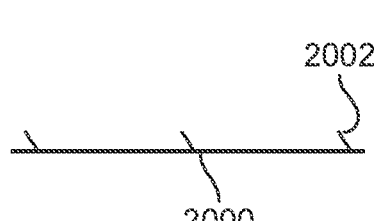
FIG. 19  FIG. 20

FIDUCIAL MARKER FOR ONCOLOGICAL AND OTHER PROCEDURES

CLAIM OF PRIORITY

The present application is a continuation of U.S. patent application Ser. No. 18/166,393 filed on Feb. 8, 2023, which application is a continuation of U.S. patent application Ser. No. 17/817,115 filed on Aug. 3, 2022, now U.S. Pat. No. 11,602,642, which is a continuation of U.S. patent application Ser. No. 16/791,410 filed on Feb. 14, 2020, now U.S. Pat. No. 11,464,998, which is a non-provisional of, and claims the benefit of US Provisional Patent Application Nos. 62/805,595 filed Feb. 14, 2019, and 62/943,464 filed Dec. 4, 2019; the entire contents of each is incorporated herein by reference.

CROSS-REFERENCE TO RELATED PATENT DOCUMENTS

This patent application is also related to U.S. patent application Ser. No. 16/160,229 filed on Oct. 15, 2018; the entire contents are incorporated herein by reference.

BACKGROUND

After certain surgical procedures, patients often require radiation therapy to irradiate any remaining diseased or damaged tissue such as cancer cells or excessively dividing cells near the site of surgery. This radiation therapy occurs after abnormal tissue is removed and the surgical cavity is closed. Markers may be used to help delineate where the removed abnormal tissue was to aid the physician in directing the radiation therapy.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 17 shows another example radiopaque marker pattern.

FIG. 18 shows an example of a radiopaque marker.

FIG. 19 shows an example of another radiopaque marker.

FIG. 20 illustrates an example of an anchor on a radiopaque marker.

DETAILED DESCRIPTION

Figures 1A, 1B:
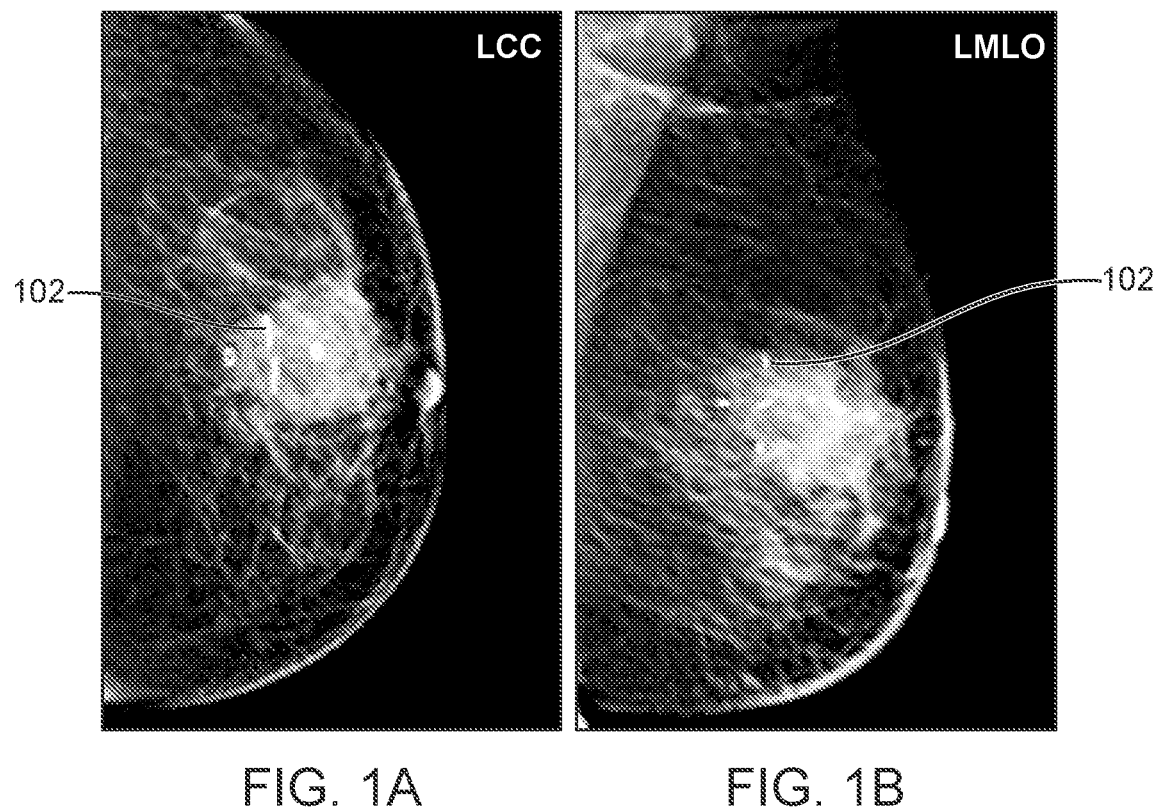
FIG. 1A illustrates a left cranio-caudal radiographic view of a traditional radiopaque marker in tissue.
FIG. 1B illustrates a left mediolateral oblique radiographic view of a traditional radiopaque marker in tissue.

After certain surgical procedures, patients may require radiation therapy to irradiate any remaining cancer cells or excessively dividing cells near the site of surgery. This radiation therapy occurs after abnormal tissue is removed and the surgical cavity is closed. However, after the cavity is closed, it is extremely difficult for a radiation oncologist to gauge the actual extent of the original tumor and the subsequent tumor bed especially when there is a complex closure of the incision. This manipulation of tissue is typically referred to as tissue re-arrangement where a portion of the closure moves in various planes in a non-symmetric closure. This is particularly common in soft tissue surgical procedures. Since radiation target/treatment planning is typically performed using x-ray based imaging after the soft tissue has been closed, the imaging often does not delineate the precise location where malignant or otherwise diseased tissue was removed and when radiation therapy to the tumor bed may be required. If radiation treatment is not necessary, it still may be beneficial to mark the surgical cavity for future monitoring and follow up of the patient.

Inaccurate representation of the tumor bed causes uncertainty, thus leading to less precise targeting/administration of radiation to the exact area of interest and potential irradiation of healthy tissue. As a result, benign tissues unnecessarily receive an increased dose of radiation therapy, the area of radiation treatment can be unnecessarily large, and the tumor bed can receive too little radiation therapy. A need therefore exists to more effectively mark the original tumor bed to allow the radiation oncologist to easily and precisely visualize the extent of the original tumor bed cavity.

After some surgeries, a post-operative fluid filled pocket can form that this is referred to as a seroma. A seroma is a pocket of fluid that typically forms after an injury, most commonly after a surgical procedure in the area where tissue was removed such as a tumor. Seromas are filled with serous fluid which may be a pale yellow, transparent fluid that contains protein, but no blood cells. Seromas are particularly common after breast surgery. While they are common, surgeons and patients prefer to avoid this complication.

Currently, various methods are used by radiation oncologists to attempt to radiographically identify the tumor bed cavity. The most common methods include visualizing a seroma that may form within the tumor bed and visualizing surgical clips or metallic fiducials ("seeds") which may be placed along the tumor bed.

A seroma may or may not be present, may represent only part of the tumor bed, or may involve an area much larger than the tumor with inclusion of the entire surgical cavity (e.g., if the incision was much larger than the actual tumor). Therefore, the seroma might not represent the true tumor bed size and location, and the seroma might lead a radiation oncologist to inaccurately plan the radiation treatment location and size. As a result, healthy and/or benign tissue may be irradiated unnecessarily, and cancer cells remaining in the tumor bed can be missed by the radiation therapy. In addition, numerous clinical papers have repeatedly proven that the size of seroma changes over time. Since most radiation treatments occur many weeks following surgery, a high probability exists that the size of the seroma may not clearly identify the actual tumor bed.

Vascular clips, that are typically used for hemostasis applications are commonly used to mark the cavity. With surgical clips or seeds, the surgeon places these markers in the tumor bed during or after excision of the tumor. They can be placed anywhere with a goal to identify the margins where surgical planes are defined as superior (towards the head), inferior (towards the feet), medial (towards the center), lateral (towards the side), anterior (towards the front), and posterior (towards the back). However, the fundamental issue with clips or seeds is that they only define a single point and not a plane. Thus, many clips or seeds are placed to provide true plane definition. Numerous clinical papers state that a minimum of 4-5 clips need to be placed in order to provide some certainty of the cavity definition. Numerous clinical papers also report that clips or seeds can migrate relatively frequently. Since they are small, attaching them to tissue is not guaranteed and when the tissue is manipulated, the clips or seeds can detach and then simply "float" in the seroma cavity.

FIGS. 1A-1B illustrate the use of a commercially available rigid, absorbable frame which includes integrated radiopaque markers that attempts to address the migration problem. The marker 102 is a rigid, absorbable radiolucent frame with several embedded titanium radiopaque markers.

Figure 2:
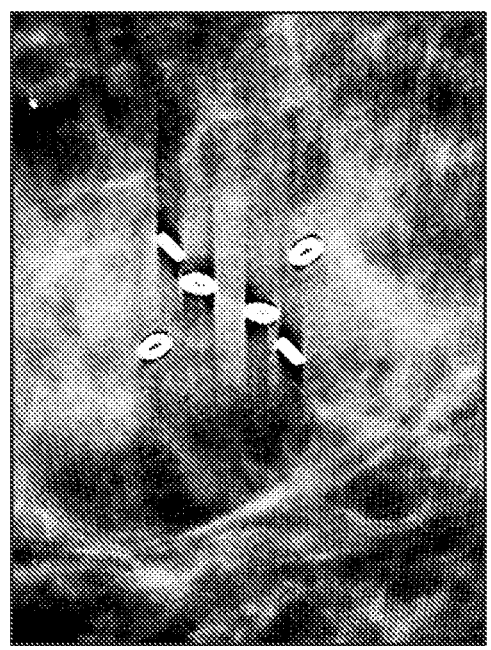
FIG. 2 illustrates imaging artifacts generated by markers in a radiograph of tissue.

FIG. 1A is a left cranial-caudal (LCC) view and FIG. 1B is a left mediolateral-oblique (LMLO) view. The frame keeps the markers from moving around. The challenge with this configuration is that the frame is rigid and palpable therefore the patient can feel it under the skin. Additionally, the individual markers which are titanium still do not address plane delineation and margin definition since there are a small number of markers and when imaged with a magnetic resonance imaging (MRI), ultrasound, x-ray or computerized tomography (CT), the metal markers may exhibit imaging related artifacts as shown in FIG. 2. These single point reference components potentially contribute to inaccuracy in target delineation for radiation therapy. The device may not always be adaptable to various sizes of tumor cavities. In certain situations its use may be restricted to relatively small cavities with a regular, basic geometric configuration.

Therefore, a need for a marker for applications such as breast lumpectomy (breast conserving surgery) exists, and the marker may be inert, implantable, durable, non-absorbable, comfortable, holds position after surgical manipulation, and radiopaque (under any imaging modality including but not limited to x-ray, mammogram, CT, ultrasound, MRI, etc.) without causing excessive imaging artifact. It may be desirable for the marker to be attached, for example threaded or otherwise secured to tissue along the entire cavity length and conform to the shape of the margin. It would eliminate artifacts, reduce or eliminate palpability, and would allow the surgeon to properly perform current era surgeries such as breast oncoplastic lumpectomy where any remaining empty void is filled by the surgeon after the tumor tissue is taken out. This is not limited to just breast surgery and other types of soft tissue procedures can benefit, such as lung, pancreas, prostate, liver, and other procedures. This is accomplished by manipulation of portions of breast tissue using re-arrangement techniques to completely close the surgical cavity without leaving a gap where a seroma can form and minimizes any skin dimpling. By attaching the elongated, continuous, radiopaque marker along the various cavity planes such as by threading the marker in tissue or clipping the marker to tissue, regardless of surgical technique employed, the radiation oncologist is be able to easily visualize postoperatively the 3-dimensional extent of the tumor bed. Visualization of the marker improves the accuracy of treatment planning for radiation therapy applied to the tumor bed. During the subsequent radiation therapy, the marker's 3-dimensional outline of the tumor bed may be easily observed during the setup for treatment. During the actual treatment, visualization of the marker's outline of the tumor bed can occur even when the bed/target is moving as a result of patient movement due to, for example, the patient's breathing, heartbeat, bowel motion etc. Based on this imaging, the delivery of radiation therapy is therefore adapted in real-time to the motion to ensure that the radiation is precisely and accurately delivered to the target tissue. Having the continuous, multi-plane marker can also allow the radiation oncologist to simply trace the marker as a planned target and use it as the boundary for radiation as opposed to drawing a larger, symmetric outline around the clips. This would dramatically reduce the toxic radiation dosage to the patient.

An example of a marker that applies to any of the markers disclosed herein and is promising includes an elongated, flexible, continuous radiopaque adaptable tissue marker as illustrated in any of FIGS. 3-19 of the present application. The marker can be formed into a filament with or without an attached needle that can be threaded through or otherwise attached to tissue. Since the marker is continuous and flexible it can be deployed/attached/threaded into a symmetric or non-symmetric shape area and/or volume. This area or volume can then be easily correlated to the radiotherapy treatment plan that closely matches the area and/or volume shape. Unlike single point markers, the radiation oncologist has to estimate the treatment plan and create or extrapolate a shape that encompasses the point markers observed. Other devices can be used to deliver the filament to the tissue, such as needle drivers, or automatic suturing devices such as suture passers. This can be done with one, single filament or multiple filament segments. The filament can be self-knotted to itself and secured/anchored to tissue or it can have features that prevent itself from slipping out of position. Features such as barbs for example or even coatings can be applied to the marker if a knotless system is desired. One can attach crimped absorbable or non-absorbable components instead of using knots to limit the filament from migrating after it has been threaded through tissue. Whether temperature-affected or moisture-activated for example, a coating can create a feature that prevents the marker from migrating. The marker may be extruded or coated with hydrogel or similar material. When hydrogel comes into contact with moisture it expands. This is an example where a hydrogel coating can be applied to a flexible marker to prevent unwanted movement of the marker that may be used with any of the marker examples disclosed herein. Also, mechanical clips can be used to attach the filament to the tissue. Coatings can also be applied to enhance visualization under specific imaging modalities such as ultrasound and MRI. Thus, a marker may be visible only under x-ray for example and a coating could be applied to the marker to make the marker visible under MRI or ultrasound. The coating does not have to be continuous, so it may just show segments of the continuous marker under one type of modality, for example MRI and in its entirety under x-ray or CT.

Other optical indicators may be added to any of the radiopaque markers disclosed herein to help a surgeon or other physician visually observe the marker. For example, the marker may be colored to allow it to be easily visualized (e.g. adding a blue color to the filament). Similarly, other coatings or indicators may be included with the radiopaque markers so that the operator may visualize and distinguish and contrast the marker from adjacent tissue.

It also may be desirable to have a marker that is only visible under x-ray or CT for example and not under MRI. Thus, there is an advantage to only having the marker visible with selective imaging modalities.

The marker can also be a paint or a gel for example that can be applied, coated or otherwise or painted onto a surface. For example, adhesive can be made to have radiopaque particles and as the adhesive is applied to one or more surfaces, the radiopaque particles will highlight the path. Again, the path will be continuous over an area.

In another example the marker can be sprayed on. The radiopaque particles can cover the entire tumor bed for example. However, over time for example certain particles can be absorbed and disappear and certain particles remain forever. Thus, any example may provide complete volume coverage for radiation planning and then disappear to provide an outline or minimal radiopaque marking that minimizes obstruction of the target treatment area during follow up imaging such as mammography. The radiopaque particles can range in shape between 0.01 microns and 500 microns. They can be encapsulated in various forms, such as glass. Various materials can be used such as silanated barium glass, silanated glass ceramic, Ba—Al—B silicate glass, SiO2, and others.

The marker can be embedded, attached or even painted onto an absorbable or non-absorbable structure such as a mesh, dermal matrix or a compliant balloon. The structure has to be transparent to radiological imaging, so the adjacent surgical planes are easily seen through the structure. So, a minimal amount of radiopaque material is visible under imaging. In some situations, no more than 10 mm wide in the shortest axis of the radiopaque marker can obstruct imaging (be radiopaque).

The filament can have various diameters. The diameters can range, for example, between 0.1 mm and 0.3 mm. Larger filaments can be developed and have diameters larger than 0.4 mm, or 1 mm or 10 mm with round or other cross-sections such as oval, square, rectangular, elliptical, etc. The tensile strength of the filament can have a range between 5 and 20 Newtons. The elongation can be greater than 50% with weight % of the radiopaque material to be between 20-40%. In addition, the elongation of the filament can be greater than 50%. The radiopaque filament can be made from various materials including polymer. The filament may remain permanently in the body, or it may be fabricated from a bioresorbable material. There are various ways to make the filament radiopaque, such as with barium sulfate, $BaSO_4$. The markers can also have metallic material or nanocrystals. As mentioned earlier, various coatings can be applied to the filament to increase friction to prevent movement. It is also feasible that various types of filament can be created with various radiopaque patterns. For example, one can imagine where a filament appears radiographically like closely spaced dots, short lines, or a continuous line. This way for example, as seen later, the surgeon can mark specific surgical planes such as posterior/lateral or lateral/superior with a uniquely identifiable marker. There is an advantage of having a continuous, flexible radiopaque marker, unlike discrete clips which have no special relationship. Also, unlike discrete clips, the continuous marker will be attached to itself and identifies a plurality of surgical planes compared to a single marker that can only identify a single point on a single plane.

If the flexible filament is extruded or drawn for example, it may have radiopaque segmental markers 1802 separated by non-radiopaque gaps 1804, as seen in FIG. 18 thereby forming a filament 1806 of any desired length. The marker may remain flexible to allow manipulation such as allowing formatting of a knot. The ends of each adjacent radiopaque segments will have fixed and non-adjustable separation. In any example it may be desirable that the gap between segments to be equal to or less than the length of each radiopaque marker segment. It may be desirable that the length of the gaps is kept minimal so that at least one radiopaque segment can be associated with a single surgical plane. The radiopaque frequency of segments could be high enough so when imaged for example they will blend together. In another example, the pattern frequency of radiopaque marker bands may be different for different markers. So, one can chose for example a dotted marker to be placed on the medial/posterior/lateral surfaces and segmented marker could be placed along superior/posterior/inferior surfaces. So, two different types of marker filaments could be deployed to distinguish the planes. The cross-sectional diameter of the radiopaque portion can be the same size as the non-radiopaque portion.

FIG. 19 shows an example of a marker where the shortest filament 1906 can consist of one flexible radiopaque marker 1902 and one non-radiopaque segment (FIG. 19). It should be noted that the flexible radiopaque marker has enough flexibility to be able to tie into at least one knot.

The elongated marker is adaptable to placement in all organ systems in a variety of patterns and techniques. Use of the marker is thus not limited to breast surgery. Applications are found in every area of the body where tumors are removed leaving a tumor bed. Tumors require delineation for targeting treatment, whether primary, nodal, or a metastatic tumor site even if a resection is not feasible, or physicians can benefit from postoperative visual guidance to direct postoperative therapy to residual malignant or non-malignant disease. Examples include treating a keloid, non-invasive breast cancer, or heterotopic ossification of a joint.

Sites beyond the breast include but are not limited to the lung, colon, rectum, bladder, prostate, esophagus, brain, head & neck, muscle, skin, vasculature, and all other areas of potential disease. For example, a physician can mark the location where vessels and nerves are connected to provide future imaging targets for radiation therapy. The marker can be used to outline the location of where a radical prostatectomy, lymph node dissection, sarcoma resection, or head & neck surgery with reconstruction has occurred, especially since for tumor bed sites such as these, postoperative radiation therapy is routinely required to treat residual disease in the operative bed. The marker can be used to identify a bronchial anastomosis, esophagogastric, or the colorectal anastomosis at risk for a local recurrence after resection of an intervening tumor. Importantly, none of these sites after surgery is accurately visualized radiographically without a marker. As a result, radiation therapy cannot be accurately planned or precisely delivered, surrounding normal tissues receive unnecessary radiation dose, and the target region can receive too little dose.

In general terms the continuous radiopaque filament may extend within one or more adjacent planes and/or between adjacent planes. The filament can start on any of the planes by attachment method such as by suturing, clipping, or other means. The filament may extend parallel to the starting plane until an adjacent plane is reached. Then when the adjacent plane is reached, the filament may turn in a different direction along the adjacent plane, being attached again in a parallel fashion to that plane. This can continue on some or every adjacent plane as the filament reaches it and turns.

A number of examples of markers are disclosed herein.

Figure 3:
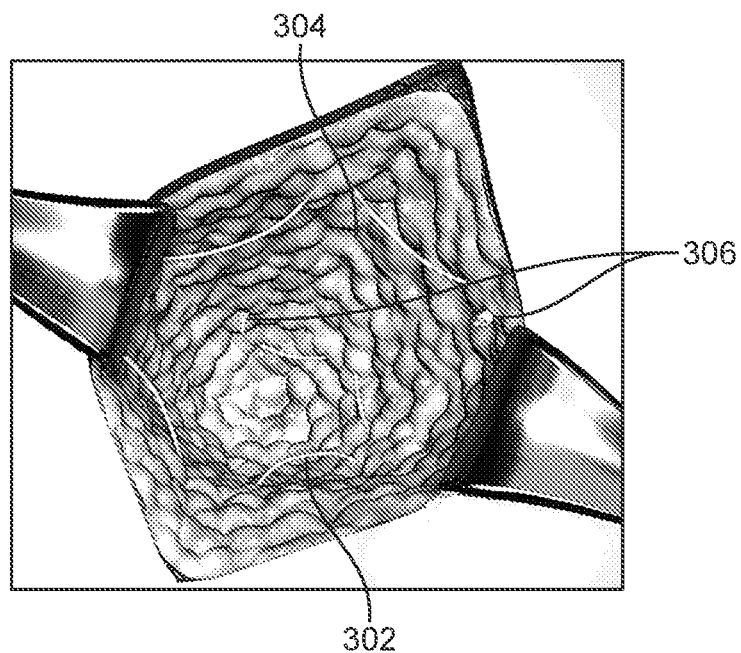
FIG. 3 illustrates a radiopaque marker in a tissue cavity.

FIG. 3 shows an example of a marker 302. The marker 302 is threaded from the bottom (posterior) of the cavity 304 up to the top (anterior) of the cavity 304 in one or multiple continuous paths across a plurality of surgical planes that are stacked on top of one another and substantially parallel to one another or may even cross. The marker is threaded continuously and follows the contours of the cavity, extending continuously partially or completely around the perimeter of the cavity, optionally forming a spiral or helix around the cavity. In FIG. 3, all the planes are defined as the filament completely surrounds the cavity. The sections of the filament are shown on the inside of the cavity with gaps in between, however in those gaps, the filament is still continuous, but since it is sutured into the tissue, the filament is not observable by the naked eye but will show up on a radiograph as a continuous filament.

FIG. 3 shows the filament extending from the bottom of the cavity to the top of the cavity, but this may also be reversed from top (anterior) to bottom (posterior). It may be desirable to make sure that all the sides of the cavity are threaded from the deepest point to the highest. What may also be desirable is to only mark the portion of the cavity where the tumor was located. So, if the tumor was only at the lower portion of the surgical cavity, only that portion of the cavity would be marked and thus the upper portion or anterior portion would remain unmarked. Thus, the marker may form a continuous band in a spiral or helix in a plurality of planes in the posterior portion of the cavity and the anterior portion of the cavity may remain marker-free. In this example one can see the filament is a running thread, weaving in and out of tissue where segments of the filament are disposed on the inner surface of the cavity and other segments are unexposed and disposed in the tissue walls surrounding the cavity. It may be desirable that one surrounds the bottom portion of the tumor bed first. A small portion of the filament tail end may be left to protrude out of the tissue and while the remainder of the filament proceeds around the posterior-most (or anterior-most plane). Once the loop defining the posterior plane is completed and the filament tail is reached, the filament and the filament tail may be knotted together. Alternatively, a knot may be formed in the suture filament end that anchors that end in tissue without requiring knotting with another portion of the filament and prevents movement of the filament. The filament may then proceed upward (or downward if you started at the anterior plane) with a running filament in a spiral pattern. The tied-off loop or knot will secure the filament at the starting end of the cavity and it will not move as it is threaded upward. A single knot or multiple knots can be self-knotted at any location around the marker depending on the tissue type to eliminate slippage of the knot and filament so the marker is firmly anchored in place. Once the filament reaches the desired height or position, the filament is tied off with another knot or knots to secure it at the opposite end, in this example the top of the cavity assuming the filament started at the bottom of the cavity. The posterior knot 306 and anterior knot 306 are shown in FIG. 3. The same result may be obtained by suturing in shorter segments instead of a continuous spiral where there are breaks or even multiple discrete rings may be used. However, still having a continuous flexible filament adjacent to plurality of planes. It is also feasible that instead of having knots to tie off the loops, the filament can be attached via clips or other techniques that rely increasing friction between the filament and the tissue to reduce movement such as those disclosed herein. It is assumed that instead of bottom to top, the user may choose to create a path from side to side, (example lateral to medial) or in any other preferred orientation or direction.

The following figures illustrate perspective diagrams showing the filament pattern described above in FIG. 3. These figures only show cube-like openings so that the six surgical planes are easily discernable. One of skill in the art will appreciate that surgical cavities are not limited to square/rectangular cavities and any cavity shape is possible, including and not limited to oval, round and asymmetric shapes, deformed volumes and non-geometric shapes. Also, the starting points are suggested as examples. The starting point in all diagrams and ending point can be on any of the planes that are convenient for the surgeon. The following figures are merely examples.

Figure 4:
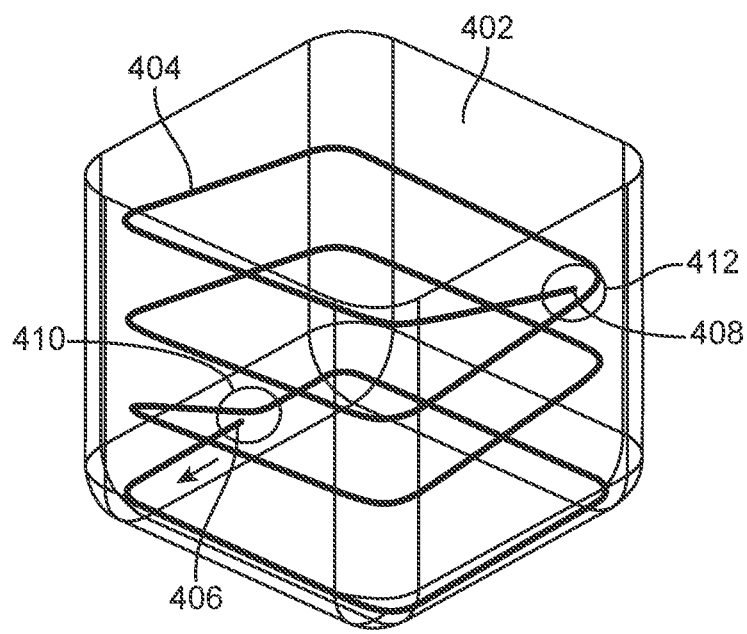
FIG. 4 illustrates an example of a radiopaque marker pattern.

FIG. 4 shows a surgical cavity 402 idealized as a square cavity where for the sake of simplicity, the bottom of the cavity is the posterior plane and the top of the box as anterior plane. The side walls represent lateral, medial, superior and inferior surgical planes where the lateral and medial planes are opposed to another and the inferior and superior planes are also opposed to one another. Therefore, the bottom plane is tissue as well as the four side wall planes. The top, or anterior plan is an open surgical incision. Filament 404 which may be any of the radiopaque markers disclosed herein starts 406 at the bottom of the cavity, which in this example is the posterior plane. A small filament tail extends out of the tissue and then is sutured in and out of the posterior tissue plane. Once the loop comes around back to the starting point, is tied off 410 with the tail (the knots going forward may be depicted by a circle) 410. The suture continuously extends from the starting point around all four walls and therefore continuously extends across the four vertical surgical planes (lateral, medial, inferior, superior) in short linear segments that may lie in a single horizontal plane that is in the posterior plane, parallel to the posterior plane, or transverse to the posterior plane, although this is not required and the suture may be sutured continuously or discontinuously around the four walls with each segment along a wall in a different plane. Once the knot is tied off, the filament turns upward toward the top of the anterior plane and proceeds in a circumferential path around the four walls of the cavity upward in the cavity anteriorly into the next plane forming another looped marker around the perimeter and then again up into the next plane and so on until the desired height is reached and then the end 408 is tied off 412 again with an adjacent portion of the filament. As mentioned, earlier, this spiral can be achieved with a continuous filament or with shorter discrete segments and additional knots. A continuous filament is a desirable pattern because it limits the number of knots, but it can also be achieved with shorter segments and more knots. In this example the segments of the radiopaque marker are linear along a wall and coupled together with a corner connector filament that joints the filament in two adjacent planes which forms a plurality of loops (square, rectangular, circular, or other shape) that are stacked on top of one another. The loops may be canted relative to the one another, parallel to one another or a combination of canted and parallel.

Thus, in FIG. 4, the continuous filament continuously extends between multiple vertical and horizontal planes and may have linear sections connected with connectors such as right-angle sections. The spiral or helical pattern is formed by the filament continuously extending around the perimeter from bottom to top of the surgical cavity and through all four walls surrounding the surgical cavity. FIG. 4 shows the suture continuously sutured to tissue in the cavity but one of skill in the art will appreciate that the suture may be sutured into and out of the tissue and therefore portions of the suture may in fact be hidden from view since the suture is under tissue, although under an x-ray the filament would show up as a continuous line.

Figure 5A:
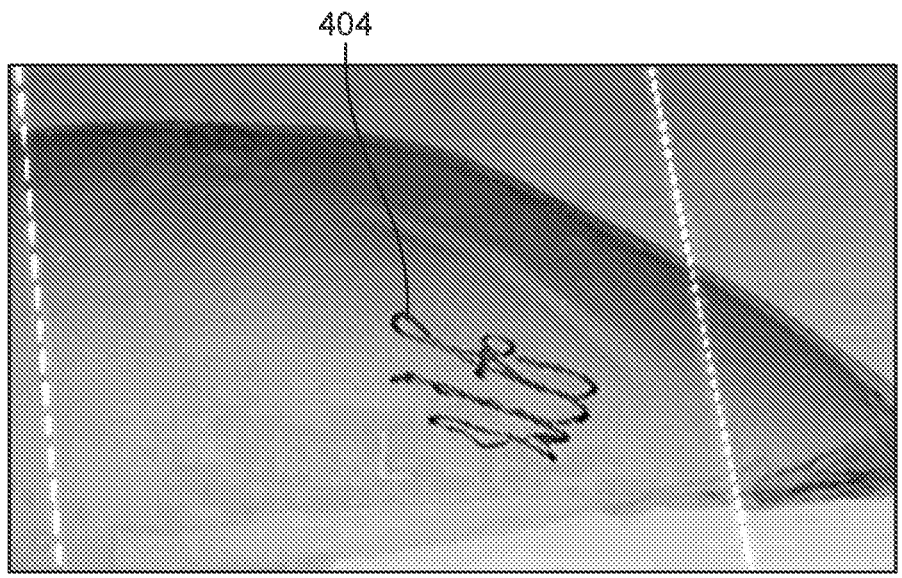
FIGS. 5A-5B illustrate different perspective views of a tumor bed cavity marked by a radiopaque filament.
Figure 5B:
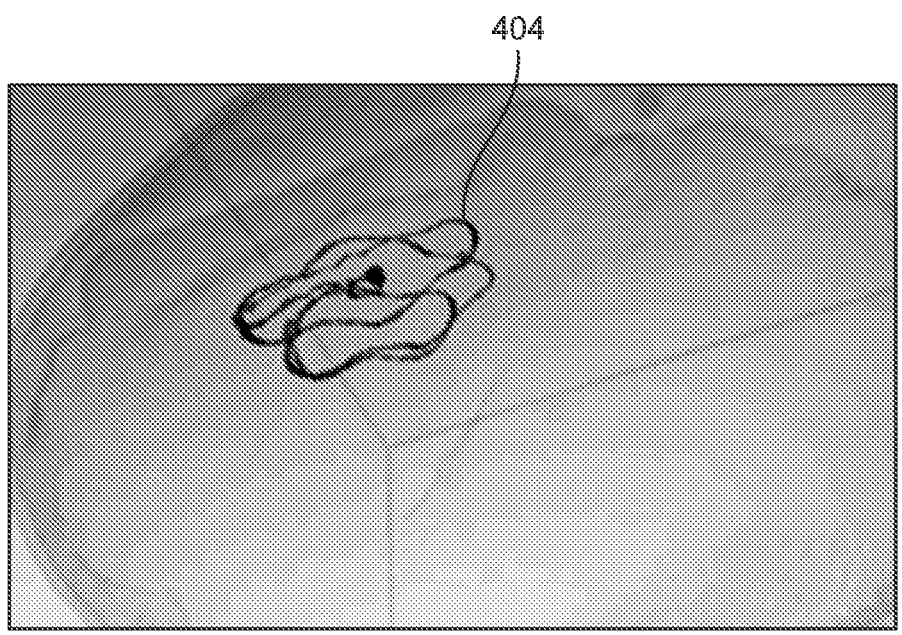

FIGS. 5A-5B show an actual 3-D imaging model derived from a CT based reconstruction of what the filaments would like from FIG. 4. FIG. 5A shows a slightly different perspective of the same 3-D reconstructed model, thus showing very clearly the shape of the tumor bed cavity from different perspectives. The tumor bed is surrounded or encompassed by the marker 404. The entire width and height are clearly depicted. Each plane, anterior, posterior, lateral, medial, superior and inferior are clearly delineated. This is a reconstructed image of multiple CT planes demonstrating the marker laid out in a spiral configuration.

Figure 6:
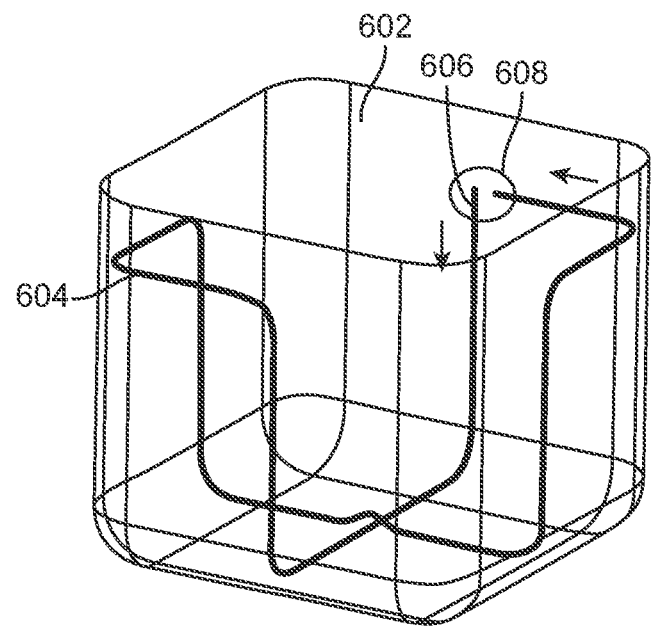
FIG. 6 shows an example radiopaque marker pattern.

FIG. 6 shows another technique for contouring the cavity 602. This may be accomplished with a single 604 or multiple filaments which may be any of the radiopaque markers disclosed herein. Here the single filament marker outlines the bottom posterior tissue surface and then the sides (superior, inferior, lateral and medial) thereby identifying multiple planes that are transverse to one another and in some situations orthogonal to one another. The filament starts 606 with a first bite on one of the walls in one vertical plane, leaving a small filament tail, then threads the filament down the wall in a substantially linear path along the vertical plane as indicated by the arrow, then turns in a transverse or approximately orthogonal direction once it reaches or is adjacent the bottom of the cavity in the posterior plane. The filament then runs across the posterior surface in a substantially linear path across the posterior plane and then changes direction transversely up the opposite wall in a substantially linear path that is substantially parallel to the first downward path and in a vertical plane that may be substantially parallel to the first vertical plane. Once the desired height is reached, the filament turns transversely (may be orthogonally) from the linear path just taken to follow a short horizontal linear path in the same vertical plane that the filament followed up, then bends transversely into an adjacent wall of the cavity into different vertical plane for a short horizontal distance until it again turns downward to extend along a linear path downward to the bottom of the cavity in the posterior plane. The filament turns again into the bottom posterior plane crossing itself until it reaches the opposite wall where the filament turns upward and extends upward along the wall in this fourth vertical plane. The filament finally turns horizontally in the fourth vertical plane, extends a short horizontal distance and then wraps around a corner into the very first vertical plane as shown by the arrow, where the filament may be tied off 608 with the tail knot to prevent from slipping through tissue, although the filament may be knotted and a knot tied with an adjacent portion of the filament. Thus, the filament defines all four vertical walls of the cavity as well as the approximate height of each wall along with the bottom of the cavity so that all six surgical planes will be visible under x-ray or other imaging. Again, this shows a single continuous path but the path may be broken down to multiple segments with multiple knots. Linear sections along a plane are coupled together between planes with a connector filament which may be a right angled corner, or any shaped connector. Additionally, as previously discussed, FIG. 6 shows the filament visible but one of skill in the art will appreciate that the filament is sutured into the tissue and therefore will have sections that are visible while other sections will be invisible to the naked eye since they are embedded in tissue, but under an x-ray will show up as a continuous line.

The filaments may be attached to a plurality of the surfaces, including more than one surface in any example. In this example the filament may be threaded in and out of the tissue, however, it can also be attached to the walls of the tissue cavity with absorbable or non-absorbable clips, or any other attachment means. The clips may be radiopaque and they can have certain markings to mark which plane they are attached, to provide differentiation amongst the various surgical planes to the doctor when the cavity is closed and viewed under x-ray, CT or other imaging schemes. The clips can also be only ultrasound visible where the marker can be only x-ray/CT visible.

Figure 7:
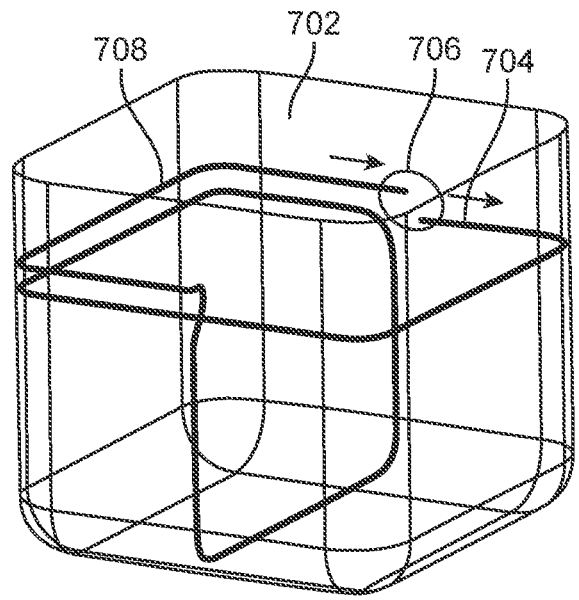
FIG. 7 shows another example radiopaque marker pattern.

The next method is illustrated in FIG. 7, where contouring the cavity 702 with a radiopaque marker 708 which may be any of those disclosed herein, includes starting 704 on one of the vertical planes (leaving a filament tail to eventually tie off to) and running a continuous or discontinous loop threading through all four adjacent planes as well as a plane in the bottom of the cavity. First, the marker starts 704 in a wall of the cavity in a vertical plane and extends a short linear distance horizontally until it passes into the adjacent vertical plane and extends along the second vertical plane in a horizontal linear continuous path. The filament (also referred to herein as the radiopaque marker or marker) then passes into a third wall or third vertical plane and extends along that plane in horizontal manner until it passes into the fourth vertical plane, again in a continuous or discontinuous path then back into the original first vertical plane. The filament may extend partially along the first vertical plane up to but not past the starting point 704 where it may be sutured 706 to the tail at the start 704, or it may extend anywhere before, after or to the starting point 704 forming a loop. Also, the filament at the start 704 may be knotted to provide an anchor either alone or in conjunction with being tied to the tail. The loop may be in a plane that is parallel or transverse to the bottom of the cavity. Once the marker extends at least partially long the first vertical plane in a horizontal manner, the marker then turns downward to extend down the first vertical plan in a linear path until it hits the bottom of the cavity in the bottom plane or adjacent to it. Again this may be a continuous or discontinuous path. When the marker hits the bottom plane or is adjacent the bottom plane, the marker then turns directions again and passes along the bottom of the cavity in the bottom plane in a continuous or discontinuous manner and in a linear path to cross the bottom of the cavity until the marker comes to the third vertical plane where the marker then turns and extends upwardly in that plane and it may or may not cross over the first horizontal segment in that plane. The marker then turns and extends horizontally along the third plane, crosses into the fourth vertical plane and extends across the fourth vertical plane in a continuous or discontinuous linear path and then turns again into the first vertical plane where the marker extends in a linear continuous or discontinuous path horizontally toward the start 704 and the tail and marker may be tied together. Thus, the marker extends through the perimeters of the cavity allowing a physician to visualize the cavity under x-ray later on.

As previously mentioned, the entire path can be done in multiple segments with multiple knots joining the segments instead of just a single continuous segment and single knot. The filament can be threaded/sutured into and out of the tissue, or attached via mechanical means like clips.

Figure 8:
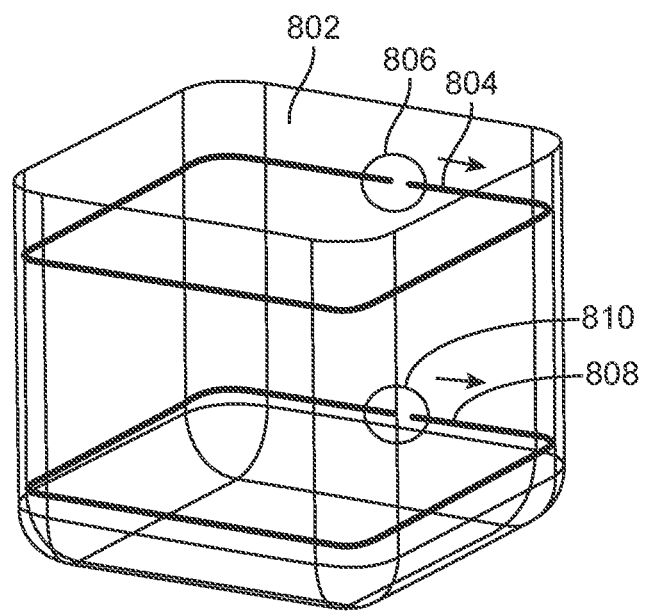
FIG. 8 shows another example radiopaque marker pattern.

FIG. 8 show an example where two filaments (or markers) which may be any of those disclosed herein are used to outline two horizontal planes in a surgical cavity 802 or other cavity. The technique uses two loops, one on the posterior plane and one on the anterior plane, or any other two planes such as a medial and lateral plane, or a superior and inferior plane. First, the filament starts 804 on a wall of the cavity in a vertical plane, extends horizontally along that plane, turns into an adjacent cavity wall and vertical plane, extends horizontally along the second vertical plane until it turns again into a third cavity wall and third vertical plane. The marker extends linearly and horizontally along the third vertical wall until it turns and extends horizontally along the fourth cavity wall or fourth plane. The marker extends linearly and horizontally along the fourth plane and then turns and crosses back into the first plane where the end of the filament is tied 806 with a tail of the filament at the start 804. Here the filament is continuous around the cavity perimeter but it may be discontinuous. Additionally, the marker forms a loop around the perimeter and loop may be in a plane that is parallel or transverse to the plane of the bottom of the cavity.

Similarly, a second loop is formed below the first loop. The marker starts 808 and extends around the cavity perimeter and through all the vertical planes defining the walls of the cavity until the marker is tied 810 off with the filament at the start 808, substantially similarly as described with respect to the first loop. The two loops may lie in planes that are parallel to one another, or transverse to one another. The loops may lie in planes that are parallel or transverse to the bottom of the cavity. Also, the loops may be continuous loops or they may be formed discontinuously by multiple segments disposed around the perimeter. A segment may be disposed in one plane, two planes, three planes, four planes, five planes, six planes, or more than six planes.

The loops may be placed anywhere along the cavity but in one example the loops are disposed as close to the top and as close to the bottom of the cavity so that the surgeon can easily determine the depth of the cavity. Using two loops also delineates all six surgical planes. The filament may be threaded, clipped, or otherwise attached to the tissue.

Figure 9:
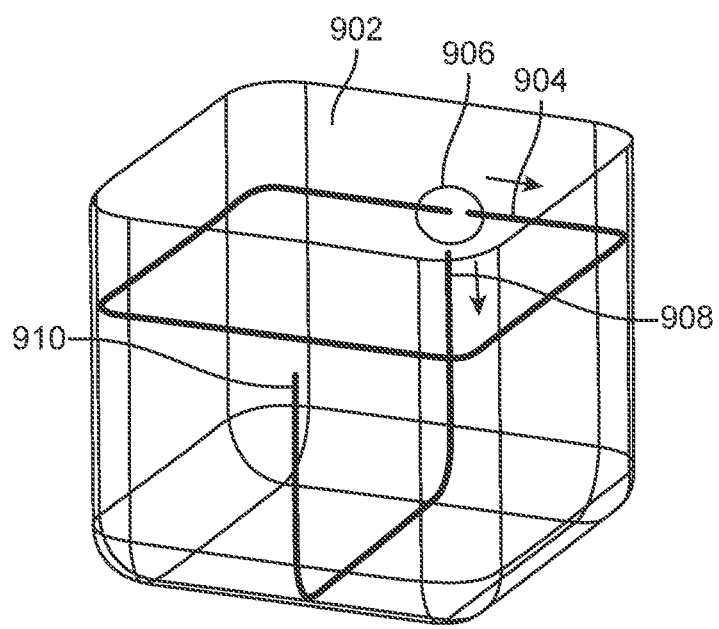
FIG. 9 shows another example radiopaque marker pattern.

FIG. 9 shows another example that uses two separate filaments to mark a cavity 902. The first filament generally takes the same form as any one of the loops in FIG. 8 above. Here, the marker starts 904 horizontally extending across a first vertical plane until it crosses over into the second vertical plane and extends horizontally across the second vertical plane until crossing into the third vertical plane which may be opposite to the first vertical plane. The marker extends horizontally along the third vertical plane until it crosses into the fourth vertical plane, extends horizontally along the fourth vertical plane and then crosses back into the first vertical. It extends horizontally along the first vertical plane until it reaches a tail at the starting point 904 and the two ends can then be knotted together to form a closed loop. The loop may be formed by a continuous linear path. The ends may not be knotted together and thus an open loop may also be formed. The loop may be parallel or transverse to the plane of the bottom of the cavity and allows easy visualization of the top of the cavity which may be the anterior surgical plane.

A second marker starts 908 in the first vertical plane, just inferior to the knot 906 and extends linearly downward along the first vertical plane until it crosses into the bottom cavity plane and extends linearly along the bottom cavity plane. The marker continues across the bottom cavity plane until it crosses into the third vertical plane opposite the first vertical plane. The marker extends upward linearly along the third vertical plane and may stop 910 either inferior to or superior to the first loop. The ends of the filament are not knotted together. The second partial loop may be orthogonal to the first loop or transverse thereto and further facilitates identification of the two vertical planes and the bottom of the cavity which may be the posterior plane.

In either loop of FIG. 9, the marker may be sutured into tissue or otherwise attached to the tissue such as with clips or other techniques known in the art. Similarly, the example of FIG. 9 shows that the two loops are formed with a continuous linear filament but this may also be formed with discontinuous segments. Also this marker pattern allows a physician to visualize the height of the tumor bed and identifies the posterior plane. The start 908 of the second loop may be coupled to the first loop and also optionally the end 910 of the second loop may also be attached to the first loop by knotting them together, clipping or using other attachment techniques.

Figure 10:
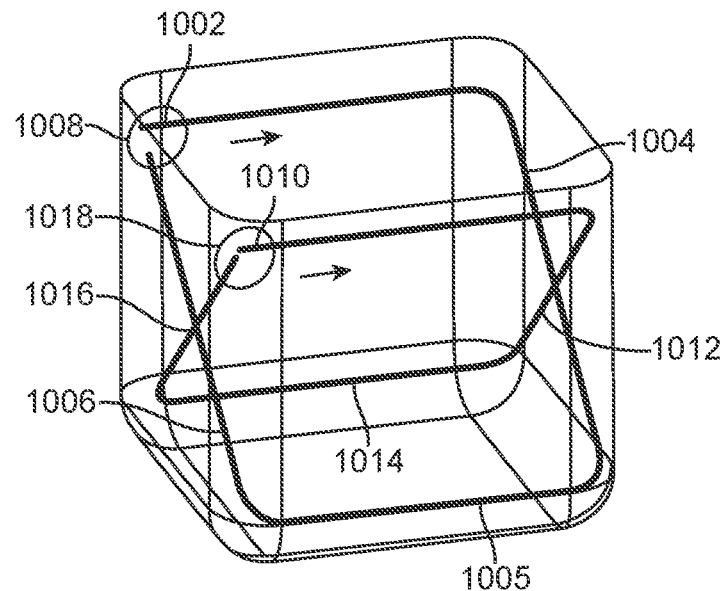
FIG. 10 shows another example radiopaque marker pattern.

Another pattern could be created by simply crossing the planes as seen in FIG. 10. In this example the radiopaque marker or filament may start 1002 in one upper portion of a vertical plane and extend horizontally across that plane in a linear path until the filament crosses into an adjacent vertical plane. The filament then curves downward and extends in a diagonal linear path 1004 across the second vertical plane toward the bottom of the cavity where the filament then turns into a third vertical plane and passes linearly and horizontally 1005 across the bottom of the third vertical plane adjacent the bottom of the cavity until reaching a fourth vertical plane. The filament extends upwardly and linearly in a diagonal path 1006 from the bottom of the cavity in the fourth vertical plane and crosses to an opposite upper region of the fourth vertical plane adjacent where the filament started in the first vertical plane. The two filament ends may then be knotted 1008 together forming a closed square or rectangular loop that is canted in the cavity. Similarly, a second square or rectangular loop may be formed in the cavity. The second loop starts 1010 with a filament in an upper portion of the third vertical plane (opposite the first vertical plane) and extends linearly and horizontally along the third vertical plane until crossing into the second vertical plane where is then turns and extends diagonally downward 1012 to the opposite side of the second vertical plane near the bottom of the cavity. The filament turns again into the first vertical plane and extends linearly and horizontally 1014 across the bottom of the first vertical plane until reaching the fourth vertical plane where the filament then extends vertically and diagonally 1016 across the fourth vertical plane until ending adjacent the starting point where the two ends may be knotted 1018 together to form the closed loop. The two loops therefore form an "X" pattern in the cavity and highlight the walls of the cavity, and the upper and lower locations of the cavity. This also creates a plane that is angled from the anterior to posterior surfaces. The pattern may also be produced using segments of markers disposed on the same path.

As mentioned earlier, an oncoplastic lumpectomy surgically brings tissue planes together to eliminate the physical void created when breast tumor tissue ("lump") is removed. It should be appreciated that when the cavity is closed, the previously attached filament can move with the tissue as the tissue is moved inward or during normal tissue movement. Unlike rigid markers mentioned earlier that are not deformable as the cavity moves, examples of the filament described herein move with the cavity. Described below are examples showing how opposing walls are brought in/re-approximated. This shows how two opposing walls are brought in, however it is possible that all four walls are moved at different heights to fill in the void left by the tumor tissue. Although the walls are moved, the originally placed marker can move with the walls.

Figure 11:
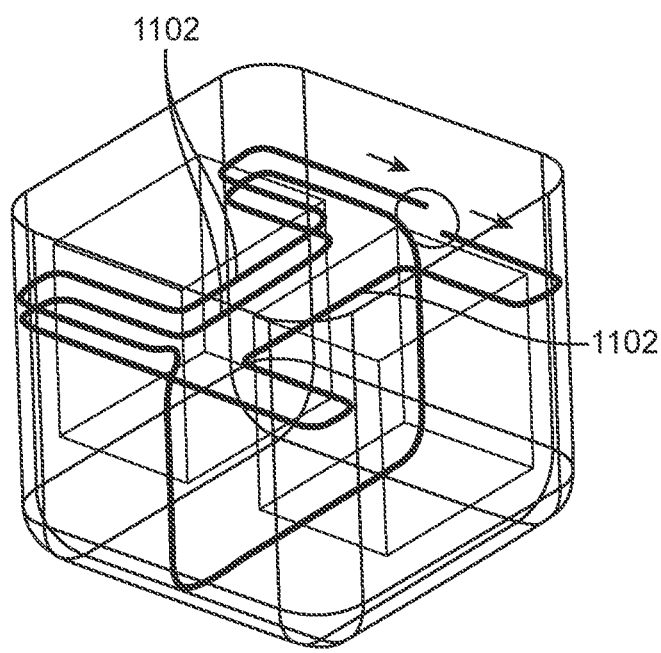
FIG. 11 shows another example radiopaque marker pattern.

FIG. 7 depicts how the marker is originally attached to the walls of a cavity and FIG. 11 shows how the marker deforms with the tissue walls when they are apposed with one another. In FIG. 11, markers 1102 in opposite vertical planes are pulled in toward one another as the tissue in those walls are apposed with one another to close the cavity. The marker position of the other filaments remain substantially the same as originally described in FIG. 7 since there is substantially no other tissue movement. The filament now outlines the tumor bed once the tissue planes have been moved.

FIG. 11 may be idealized but does emphasize that the center portion of opposing walls move inward toward one another while the outer portions of opposing walls may move inward less and thus there is corresponding movement of the marker.

As demonstrated, the filament represents the delineated margins regardless of surgical procedure performed after tumor excision and marking of the tumor bed with the filament.

Figure 12:
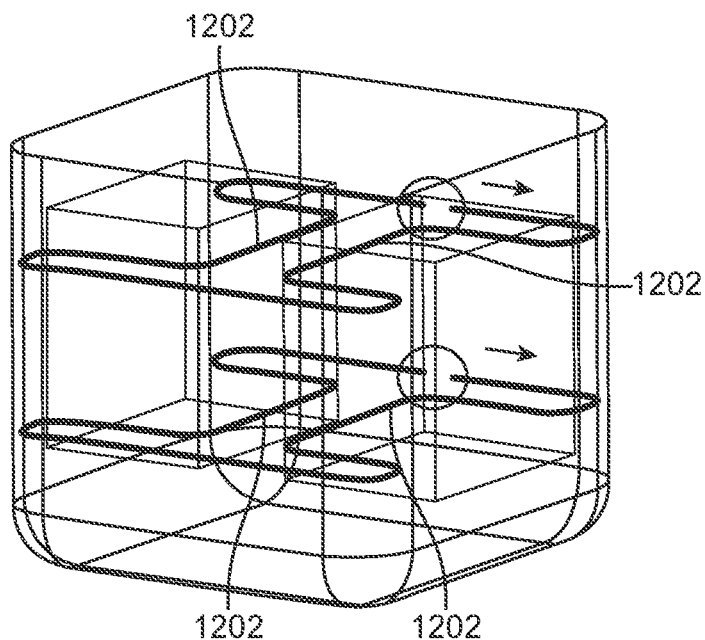
FIG. 12 shows another example radiopaque marker pattern.

FIG. 11 and FIG. 7 represent the same marked tumor bed. FIG. 7 is the radiographic depiction with no tissue re-approximation after tumor excision and filament placement. FIG. 11 is a radiographic example of tissue re-approximation or oncoplastic surgery after tumor excision and filament placement. As mentioned earlier this only shows two walls being moved, however this can be done with all walls. Here the filament path follows any movement of the tissue planes. FIG. 12 shows another example how the filament outlines the moved tissue.

FIG. 8 shows the tumor bed prior to tissue movement and after tissue movement in FIG. 12. As can be seen in FIG. 12, the opposite planes were moved and the filament outlines the path 1202 of the moved tissue compared to the original path as depicted in the original FIG. 8. Again, the filament follows the path of the tissue that is moved.

It is feasible that the physician or surgeon can leave some slack when the filament is attached to the tissue in any of the examples, especially when the tissue has to be moved so that the filament can follow the new path. The filament can also be pulled to close the tissue together and act as a suture. So if the filament is brought around the tumor bed, it may be pulled up and cinched so the cavity closed.

Figure 13:
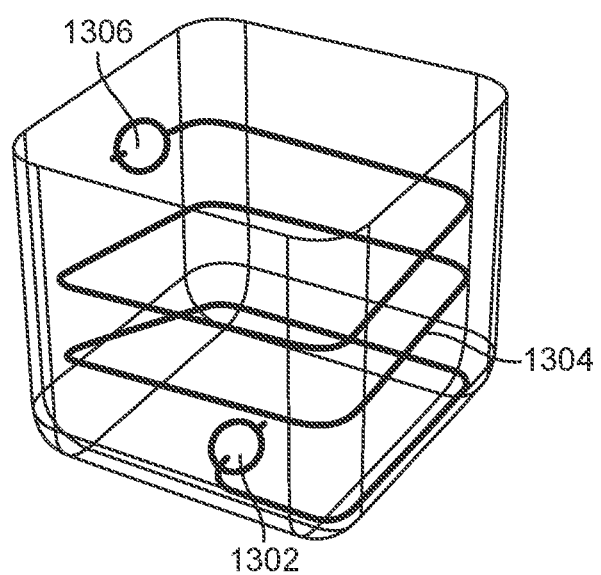
FIG. 13 shows another example radiopaque marker pattern.

In yet another example, as seen in FIG. 13, a new pattern can be constructed, similar the spiral shown earlier in FIG. 4. The difference is creating a small knot 1302 at the proximal end of the marker. In this example the proximal knot 1302 is used to anchor the marker at one of the surgical planes (anterior, posterior, lateral, medial, superior or inferior). In this example it is the posterior plane (where the top of the box represents the anterior plane). Here, the maker is inserted into tissue and pulled through all the way out until the knot prevents any further movement. This will anchor the proximal end of the marker and from here any of the patterns can be initiated. The knot is large enough so it does not slip through the tissue, especially when passing through fatty tissue. In this example, the surgeon starts the marker in the bottom of the cavity which here is the posterior plane by anchoring the marker with knot 1302. From there, the filament outlines the posterior plane by passing the marker continuously in an upwardly sloping linear path around the lateral, medial, superior and inferior planes (vertical planes) and once the surgeon is satisfied with the outline, the surgeon will begin to angle the marker towards the anterior plane and continue to traverse around all planes mentioned in an upward spiral 1304. In any of the examples disclosed herein where a tail of the filament is tied with another portion of the filament, this may be substituted with a simple knot in the filament that prevents the filament from passing through the tissue and without forming a knot with another portion of the filament.

Once the desired height is reached, instead of closing the loop as demonstrated in previous patterns and tying the loop off, a simple knot 1306 can be made on the distal end of the marker to prevent it from being pulled back. So, this example describes a proximal anchor and distal anchor. These anchors are described as just knots, however mechanical means, like clips can be used to stake the ends onto tissue. As mentioned earlier, in this or any example, the filament may be tied with another portion of the filament, or a single or multiple knots can be deployed to ensure that the filament does not slip through the tissue.

Figure 14:
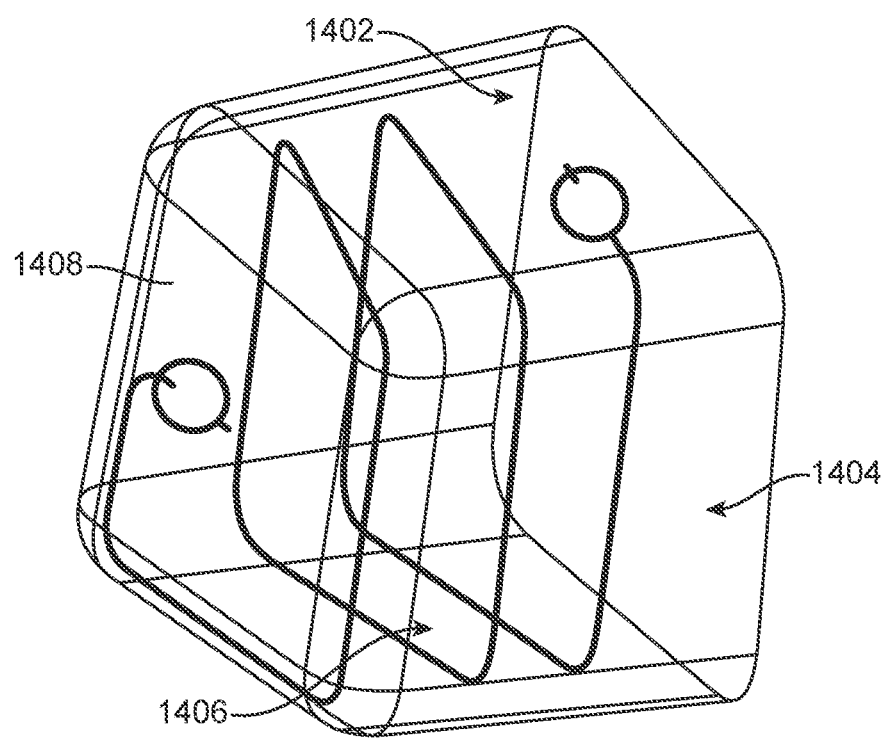
FIG. 14 shows another example radiopaque marker pattern.

The previous examples described above have assumed that markers are placed between the anterior and posterior planes as seen in all the patterns shown, however this is not intended to be limiting. Defining the surgical cavity starts at the anterior plane and extends down to the posterior plane. It is entirely possible that the cavity starts at the lateral plane 1404 and extends to the medial plane as seen in FIG. 14 which also shows the anterior plane 1402 and the posterior plane 1406. So, all the patterns can be repeated, except that the pattern will be rotated to show where the access plane is, for example lateral in FIG. 14. Therefore, one of skill in the art will appreciate that the marker(s) may start, end or otherwise be placed in any plane and hence the examples are not limited to specific planes.

Figure 15:
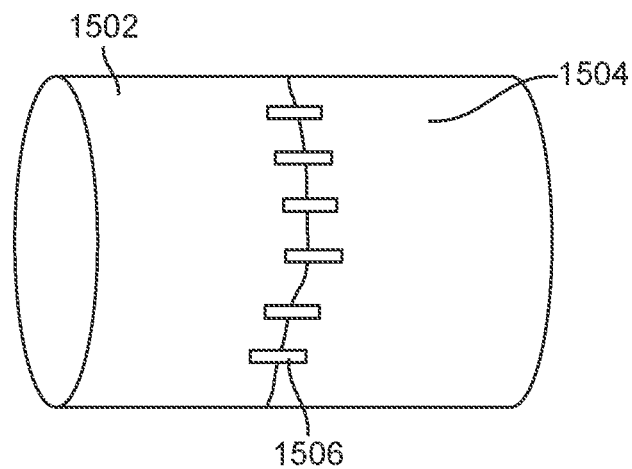
FIG. 15 shows another example radiopaque marker pattern.

One advantage of a continuous radiopaque marker filament is that it can be used as a suture to bring and hold tissue together as illustrated in FIG. 15. This is helpful when internal structures are brought together. The marker can be imaged and thus show how well the closure has held up. So post-operative images can be taken over time to see if the marker has now changed in shape (deformed) thus depicting how well the tissue has re-approximated and stayed together.

FIG. 15 shows to ends of tissue 1502, 1504 which are apposed with one another and then sutured 1506 together. The suture may be any of the examples of radiopaque sutures or markers disclosed herein. The suture will then be visible under x-ray.

Also, markers may be used to identify tissue or used as targets for external beam irradiation. Another value of the marker is that it can be used with internal radiation technologies such as brachytherapy. Since the cavity is not filled with a marker and only the outline is marked, surgical catheters that deliver internal radiation such as accelerated partial breast radiation can be used in conjunction with the continuous radiopaque marker. A pattern, similar to FIG. 6 can be deployed for example with a brachytherapy insertion, where the anterior plane opens up to deliver the brachytherapy catheter. Any filament or marker may be used in any example of a pattern with or without brachytherapy.

Figure 16:
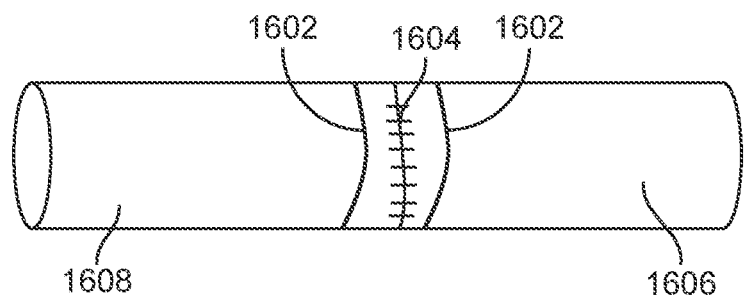
FIG. 16 shows another example radiopaque marker pattern.

FIG. 16 shows another example where applying the markers disclosed herein may be applied to other anatomical structures. Rather than delineating the tumor bed with filament threads inside the bed, this method illustrates the concept of using loops or segments of filament thread 1602 to mark the site of an anastomosis 1604 following removal of diseased tissue along a tubular or longitudinal structure where an opening is created when disease intervening along such a structure is surgically removed. The open ends 1606, 1608 are surgically reconnected with sutures or similar methods, thereby creating the anastomosis 1604. Here the filament marker 1602 is applied to one or more sides around the anastomosis. In this example the marker is circumferentially disposed around all or a portion of the perimeter of both ends of tissue joined together.

Common examples where anastomoses are formed include a colorectal anastomosis, esophagogastric anastomosis, and bronchial anastomosis after lung resection. After surgery, an anastomosis is difficult to see with x-ray based imaging techniques routinely used to plan and target radiation therapy around the anastomosis which presents a challenge since the anastomosis is the area at highest risk of recurrence of disease. However, intraoperative placement of filament threads on either side of the anastomosis will permit the radiation oncologist to subsequently delineate the site of anastomosis that requires radiation therapy. Beyond providing the precise location of the anastomosis, the surgeon can also place the filament thread(s) in a location that will assist the radiation oncologist in other ways to better design postoperative radiation therapy. For example, based upon observations that can be made only intraoperatively, the surgeon can elect to place a loop or segment of filament thread to mark an area that should not receive a higher dose of radiation therapy than necessary (e.g., location of a critical blood supply, delicate watershed area, compromised tissue, etc.). For a small area that would benefit from visual delineation to guide postoperative therapy, a knot of filament thread would suffice. As seen in this figure a small knot is formed with the marker next to a critical structure to highlight it under imaging. The applications for using this technique can also be applied to vessels, nerves etc. The concept is to mark the area of intervention such as anastomosis for follow-up imaging. When vessels are connected, there may be interest to know the location of that anastomosis with or without radiation therapy.

FIG. 17 shows a region of tissue 1702 being treated and having sensitive tissue or an area 1704 that the physician desires to mark with a marker 1706 so that it is visible later under x-ray. That way the marked tissue may be easily identified and excluded from irradiation or other treatments later. Examples of sensitive tissue 1704 include but are not limited to those disclosed above including vessels or nerves. Any marker disclosed herein may be used as the marker 1706 in this example.

In some examples, a series of discrete markers may be used to outline the target area. The discrete markers may be short segments of the radiopaque suture filaments described herein and separated by a gap. Or a plurality of discrete radiopaque markers separated by a gap may be disposed on a continuous suture filament. The gap or distance between radiopaque markers may be equal to or less than the distance or length of the marker portions which helps form a substantially continuous line under x-ray so that the physician does not have to extrapolate where the target area boundaries are.

In some examples, the marker may be integrated into a material. The material may be injected or placed into a desired location as long as the material is transparent to the imaging modalities. The material may be three dimensional to fill a cavity. The marker should not obstruct imaging.

In any example, the radiopaque marker permits unambiguous three-dimensional visualization of the site of interest which may be a tumor bed. Visualization is achieved without requiring extrapolation or interpretation of the site borders. This is contrary to traditional markers such as clips which do require an observer to extrapolate a line or surface between discrete points. Moreover, examples of the current marker do not migrate once placed in the tissue unlike clips and other markers which can move and therefore distort visualization of the site of interest.

Some examples, the marker may be placed in the site of interest to form a lattice or mesh which allows the site to be visualized. In other examples, the marker may be placed continuously or with a plurality of discrete markers so that the marker is coaxial along its length. In other examples, the marker may be placed such that three points are placed in one surgical plane to help the observer visualize the first surgical plane, and the marker may also be placed in a second or any number of additional surgical planes with at least three points in each surgical plane to allow the observer to clearly visualize each surgical plane. The marker may be placed in the any of the permutations or combinations of the following surgical planes including the anterior, posterior, lateral, medial, superior and inferior planes.

In any example, the length of the marker may be >0.5 mm, >1 mm, >2 mm, >3 mm, >4 mm, >5 mm, >6 mm, >7 mm, >8 mm, >9 mm, >10 mm, >11 mm, >12 mm, >13 mm, >14 mm, >15 mm, >16 mm, >17 mm, >18 mm, >19 mm, >20 mm, >21 mm, >22 mm, >23 mm, >24 mm, >25 mm, >26 mm, >27 mm, >28 mm, >29 mm, >30 mm, >31 mm, >32 mm, >33 mm, >34 mm, >35 mm, >36 mm, >37 mm, >38 mm, >39 mm, >40 mm, >41 mm, >42 mm, >43 mm, >44 mm, >45 mm, >46 mm, >47 mm, >48 mm, >49 mm, or >50 mm.

In any example where there are gaps between markers, the gap distance may be <50 mm, <49 mm, <48 mm, <47 mm, <46 mm, <45 mm, <44 mm, <43 mm, <43 mm, <42 mm, <41 mm, <40 mm, <39 mm, <38 mm, <37 mm, <36 mm, <35 mm, <34 mm, <33 mm, <32 mm, <31 mm, <30 mm, <29 mm, <28 mm, <27 mm, <26 mm, <25 mm, <24 mm, <23 mm, <22 mm, <21 mm, <20 mm, <19 mm, <18 mm, <17 mm, <16 mm, 15 mm, <14 mm, <13 mm, <12 mm, <11 mm, <10 mm, <9 mm, <8 mm, <7 mm, <6 mm, <5 mm, <4 mm, <3 mm, <2 mm, <1 mm, <0.05 mm. In all cases where there is a gap, the gap must be greater than 0 mm.

Any example of a marker may include a solid core and yet still be a flexible marker that is radiopaque. The flexibility should be adequate to allow the marker to conform to the site of interest with symmetric or non-symmetric shape area or volume and also allow the marker to be tied into a knot. The marker encloses the area or volume to allow the physician to determine the treatment plan or region without requiring extrapolation of the area or volume based on the markers.

Any example may be a radiopaque, flexible marker that can be implanted permanently and attached, sutured or otherwise coupled to tissue. Any example may be a flexible, continuous, radiopaque, implantable marker that once deployed in tissue allows measurement of the area or the volume. The marker may have any of the characteristics of the markers disclosed in U.S. patent application Ser. No. 16/160,229 previously incorporated herein by reference. Any marker disclosed herein may have uniform radiopacity characteristics, or one side of the marker may have different radiopacity characteristics relative to a second side of the marker. Any marker disclosed herein may be formed into a spring element that can expand from a collapsed configuration to fill a void or surgical or other cavity.

While the devices and methods disclosed herein have primarily been disclosed with reference to use in living human tissue, one of skill in the art will appreciate that this is not intended to be limiting. The devices and methods disclosed herein may be used in animals, cadaver tissue, or other non-tissue materials. For example, a synthetic graft may use any of the devices and methods disclosed herein to mark the device prior to use. Similarly, a stent-graft or prosthetic valve having a cover and expandable frame may be assembled before implantation using radiopaque filaments to secure the cover to the expandable frame. Also, the devices and methods disclosed herein may be used on fabric or synthetic materials for training, demonstration, assembly, or other non-treatment purposes. In all the previous examples, the application of the marker may be performed in open surgery, laparoscopic surgery and even percutaneous surgery. Having the filament delivered through a laparoscopic cannula for example, such as in a standard or robotic application is entirely feasible. For example, a needle may be used that is small enough to fit through the cannula and then deployed using standard laparoscopic instruments.

Any of the examples of radiopaque markers may be used as part of system which may include other surgical instruments, radiotherapy treatment supplies such as brachytherapy, radiotherapy planning software, tumor localization solutions, tumor radiographic imaging, or other items. Examples of tumor localization solutions including wires, as well as magnetic and radiofrequency based equipment. Examples of tumor radiographic imaging equipment include x-ray, ultrasound, CT, and mammography equipment.

FIG. 20 illustrates an example of a radiopaque marker 2000 which may be any of the examples disclosed herein with anchors 2002 which may be coupled to the radiopaque marker in order to prevent movement of the marker once coupled to the tissue. The anchors 2002 may be placed at one end of the radiopaque marker, on both ends, in a middle portion, combinations thereof, or in any position along the marker. Examples of anchors may be clips, barbs, or any of the other anchor elements disclosed herein.

NOTES AND EXAMPLES

The following, non-limiting examples, detail certain aspects of the present subject matter to solve the challenges and provide the benefits discussed herein, among others.

Example 1 is a method for marking a target with a radiopaque marker, said method comprising: providing a radiopaque filament; inserting at least a portion of the radiopaque filament into tissue; extending the radiopaque filament continuously at least partially around a perimeter of the target and disposing the radiopaque filament in a plurality of surgical planes, thereby demarcating the target with the radiopaque marker.

Example 2 is the method of Example 1, further comprising disposing at least a portion of the radiopaque filament adjacent an outer surface of the tissue so that the portion of the radiopaque filament is uncovered by the tissue.

Example 3 is the method of any of Examples 1-2, wherein extending the radiopaque filament comprises continuously following a contour of a cavity with the radiopaque filament.

Example 4 is the method of any of Examples 1-3, further comprising forming one or more knots in the radiopaque filament.

Example 5 is the method of any of Examples 1-4, wherein the plurality of surgical planes comprises at least two or more of a superior plane, inferior plane, lateral plane, medial plane, anterior plane, and a posterior plane.

Example 6 is the method of any of Examples 1-5, wherein at least some of the plurality of planes are parallel to one another.

Example 7 is the method of any of Examples 1-6, wherein at least some of the plurality of planes are transverse or orthogonal to one another.

Example 8 is the method of any of Examples 1-7, wherein the radiopaque filament extends between the plurality of planes.

Example 9 is the method of any of Examples 1-8, wherein walls of the cavity form a tubular structure, and wherein the radiopaque filament extends at least partially circumferentially around the tubular structure.

Example 10 is the method of any of Examples 1-9, wherein the radiopaque filament forms a continuous line in the tissue.

Example 11 is the method of any of Examples 1-10, wherein the radiopaque filament forms a closed loop in the tissue.

Example 12 is the method of any of Examples 1-11, wherein the radiopaque filament demarcates a rectangular region or a conical region in the tissue.

Example 13 is the method of any of Examples 1-12, wherein the radiopaque filament demarcates a region of malignant, diseased or damaged tissue that has been excised from a patient.

Example 14 is the method of any of Examples 1-13, wherein extending the radiopaque filament comprises disposing the radiopaque filament in a spiral pattern in the tissue.

Example 15 is the method of any of Examples 1-14, further comprising inhibiting movement of the radiopaque filament relative to the tissue with barbs or one or more knots, disposed on the radiopaque filament, the barbs or one or more knots configured to engage with the tissue.

Example 16 is the method of any of Examples 1-15, further comprising inhibiting movement of the radiopaque filament with a coating disposed thereon that resists slidable movement of the radiopaque filament relative to the tissue.

Example 17 is the method of any of Examples 1-16, further comprising observing the radiopaque filament with radiographic imaging.

Example 18 is the method of any of Examples 1-17, wherein the radiopaque filament further comprises an echogenic coating or pattern disposed thereon, the method further comprising visualizing the radiopaque filament with ultrasound.

Example 19 is the method of any of Examples 1-18, wherein a first side of the radiopaque filament has a first radiopacity and is distinguishable from a second side of the radiopaque filament which has a second radiopacity, as viewed under radiographic imaging.

Example 20 is the method of any of Examples 1-19, wherein the radiopaque filament forms a spring element.

Example 21 is the method of any of Examples 1-20, wherein the radiopaque filament forms an expandable radiopaque marker configured to expand and fill a void left by excision of malignant, diseased or damaged tissue.

Example 22 is the method of any of Examples 1-21, wherein the radiopaque filament comprises a proximal end and a distal end, the method further comprising anchoring the proximal or distal end to tissue by knotting the proximal or distal end of the radiopaque filament.

Example 23 is the method of any of Examples 1-22, wherein both the proximal and distal ends are anchored to the tissue.

Example 24 is the method of any of Examples 1-23, wherein inserting at least a portion of the radiopaque filament into tissue comprises starting deployment of the radiopaque filament in an anterior plane and moving the radiopaque filament toward a posterior plane.

Example 25 is the method of any of Examples 1-24, wherein inserting at least a portion of the radiopaque filament into tissue comprises starting deployment of the radiopaque filament in in a lateral plane and moving the radiopaque filament toward a medial plane.

Example 26 is the method of any of Examples 1-25, further comprising tensioning the radiopaque filament thereby apposing the tissue.

Example 27 is the method of any of Examples 1-26, further comprising applying brachytherapy to the target.

Example 28 is a radiopaque marker comprising: an elongate flexible radiopaque filament visible under radiographic imaging, and wherein the radiopaque marker is disposed continuously in one or a plurality of surgical planes.

Example 29 is the radiopaque marker of Example 28, wherein the radiopaque marker extends between the plurality of planes.

Example 30 is the radiopaque marker of any of Examples 28-29, wherein the radiopaque marker is disposed in a plurality of continuous lines interconnected with arcuate connections therebetween.

Example 31 is the radiopaque marker of any of Examples 28-30, wherein the radiopaque marker comprises 20% to 40% by weight of the radiopaque material.

Example 32 is the radiopaque marker of any of Examples 28-31, wherein the elongate flexible filament has a diameter ranging from 0.1 mm to 0.3 mm.

Example 33 is the radiopaque marker of any of Examples 28-32, wherein the elongate flexible filament has a circular cross-section.

Example 34 is the radiopaque marker of any of Examples 28-33, wherein the elongate flexible filament has a diameter larger than 0.4 mm.

Example 35 is the radiopaque marker of any of Examples 28-34, wherein the elongate flexible filament has a diameter larger than 1 mm.

Example 36 is the radiopaque marker of any of Examples 28-35, wherein the elongate flexible filament has a tensile strength between 5 and 20 Newtons.

Example 37 is the radiopaque marker of any of Examples 28-36, wherein the elongate flexible filament has an elongation greater than 50%.

Example 38 is the radiopaque marker of any of Examples 28-37, wherein the radiopaque filament comprises barium sulfate.

Example 39 is the radiopaque marker of any of Examples 28-38, further comprising a coating on the elongate filament, the coating configured to increase friction of the elongate filament passing through tissue.

Example 40 is the radiopaque marker of any of Examples 28-39, wherein the elongate filament is formed into a closed loop.

Example 41 is the radiopaque marker of any of Examples 28-40, wherein the elongate filament is formed into a spiral.

Example 42 is the radiopaque marker of any of Examples 28-41, wherein the elongate filament is knotted in one or more regions.

Example 43 is the radiopaque marker of any of Examples 28-42, wherein the elongate filament comprises a plurality of segments, each segment disposed in different planes.

Example 44 is the radiopaque marker of any of Examples 28-43, wherein the plurality of surgical planes comprises at least two or more of a superior plane, inferior plane, lateral plane, medial plane, anterior plane, and a posterior plane.

Example 45 is the radiopaque marker of any of Examples 28-44, wherein the elongate filament comprises a proximal end and a distal end, the elongate filament further comprising an anchor element disposed adjacent the proximal or distal end.

Example 46 is the radiopaque marker of any of Examples 28-45, wherein the anchor element comprises a knot.

Example 47 is the radiopaque marker of any of Examples 28-46, wherein a first end of the elongate filament is configured to be disposed in an anterior plane of a patient and the elongate filament extends toward a posterior plane of the patient.

Example 48 is the radiopaque marker of any of Examples 28-47, wherein a first end of the elongate filament is configured to be disposed in a lateral plane of a patient and the elongate filament extends toward a medial plane of the patient.

Example 49 is the radiopaque marker of any of Examples 28-48, wherein the elongate filament is configured to be disposed in tissue, and wherein the elongate filament is configured to be drawn to itself when tension is applied thereto, thereby apposing the tissue.

Example 50 is a system for treating a patient, comprising the radiopaque marker of any of Examples 28-49; and one or more brachytherapy irradiation elements.

Example 51 is a radiopaque marker comprising a plurality of radiopaque segments coupled to a filament with gaps disposed between adjacent radiopaque segments, wherein the gap is <50 mm.

Example 52 is a radiopaque marker comprising a plurality of radiopaque segments disposed in a plurality of planes, wherein the plurality of segments are coaxial with one another.

Example 53 is a radiopaque marker, comprising a plurality of radiopaque segments disposed in a plurality of planes forming a lattice or mesh of radiopaque segments allowing visualization of a target region without extrapolation of the plurality of radiopaque segments.

Example 54 is a radiopaque marker comprising at least three radiopaque segments disposed in a first plane and at least three radiopaque segments disposed in a second plane.

Example 55 is a radiopaque marker comprising a marker element having a solid core that is flexible and radiopaque, wherein the marker element is flexible enough to allow a knot to be tied therewith.

Example 56 is a radiopaque marker comprising a flexible radiopaque element which can be deployed into symmetric or non-symmetric shapes, areas, or volume and into at least a single plane.

Example 57 is a method for marking a target with a radiopaque marker, comprising providing a radiopaque filament; inserting at least a portion of the radiopaque filament into a non-living material; and extending the radiopaque filament continuously at least partially around a perimeter of the target and disposing the radiopaque filament in a plurality of planes, thereby demarcating the target with the radiopaque marker.

In Example 58, the devices, systems or methods of any one or any combination of Examples 1-57 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects. The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A radiopaque marker device for marking a target tissue surrounding a surgical cavity formed during a surgical procedure, comprising:
   a spring element disposed in a closed loop having a perimeter, the spring element comprising a first elongate flexible radiopaque filament disposed in a closed loop, wherein the spring element is observable under radiographic imaging,
   wherein the spring element is configured to expand from a collapsed configuration to an expanded configuration,
   wherein the radiopaque marker device is configured to be implanted into the surgical cavity during the surgical procedure,
   wherein the perimeter of the closed loop is radiopaque and configured to engage the target tissue surrounding the cavity, and
   wherein the radiopaque marker device is configured to move with the target tissue during movement thereof.

2. The radiopaque marker device of claim 1, wherein the spring element in the expanded configuration is adapted to fill a void or the surgical cavity.

3. The radiopaque marker device of claim 2, wherein the first elongate flexible radiopaque filament is configured to move with tissue as the tissue is moved to close the void or the surgical cavity.

4. The radiopaque marker device of claim 2, wherein the first elongate flexible radiopaque filament is configured to continuously follow a contour of a wall of the void or the cavity.

5. The radiopaque marker device of claim 1, wherein the first elongate flexible radiopaque filament comprises a coating.

6. The radiopaque marker device of claim 5, wherein the coating comprises a hydrogel or wherein the coating increases friction on the first elongate filament and limits movement of the first elongate filament in tissue.

7. The radiopaque marker device of claim 1, further comprising a hydrogel coupled to the first elongate flexible radiopaque filament.

8. The radiopaque marker device of claim 1, further comprising an anchor, wherein the anchor is configured to be coupled to the first elongate radiopaque filament.

9. The radiopaque marker device of claim 8, wherein the anchor comprises a clip and wherein the clip is absorbable, or wherein the clip is echogenic and visible under ultrasound.

10. The radiopaque marker device of claim 8, wherein the anchor is configured to attach the first elongate radiopaque filament to tissue, the tissue disposed in one or more surgical planes.

11. The radiopaque marker device of claim 1, wherein the first elongate radiopaque filament is configured to be threaded or clipped to tissue.

12. The radiopaque marker device of claim 1, wherein the first elongate radiopaque filament is bioresorbable or non-absorbable.

13. The radiopaque marker device of claim 1, wherein the first elongate radiopaque filament comprises a metal.

14. The radiopaque marker device of claim 1, wherein the spring element further comprises a second elongate radiopaque filament.

15. The radiopaque marker device of claim 14, wherein the first elongate radiopaque filament has a first radiopaque pattern and the second elongate radiopaque filament has a second radiopaque pattern different than the first radiopaque pattern, such that the first and second radiopaque patterns are distinguishable from one another under radiography.

16. The radiopaque marker device of claim 1, wherein the first elongate radiopaque filament has two ends knotted together to form the closed loop.

17. The radiopaque marker device of claim 1, wherein the spring element is free of material disposed inside the perimeter of the closed loop.

18. A method for marking a target tissue surrounding a surgical cavity, the method comprising:
  providing a spring element in a collapsed configuration, wherein the spring element is disposed in a closed loop having a perimeter and comprises a first elongate flexible radiopaque filament disposed in a closed loop;
  performing a surgical procedure to form the surgical cavity:
  disposing the spring element adjacent the target tissue during the surgical procedure; and
  self-expanding the spring element from the collapsed configuration to an expanded configuration, wherein the perimeter of the closed loop is radiopaque and in the expanded configuration the perimeter of the spring element abuts the target tissue surrounding the cavity, and
  wherein the spring element is configured to move with the target tissue during movement thereof.

19. The method of claim 18, further comprising observing the spring element under radiographic imaging.

20. The method of claim 18, wherein the target tissue defines a void or the surgical cavity, and wherein the spring element is disposed in the void or the surgical cavity to fill demarcate a boundary of the void or the surgical cavity.

21. The method of claim 20, further comprising closing the void or the surgical cavity thereby causing the first elongate flexible radiopaque filament to move with tissue surrounding the void or the cavity.

22. The method of claim 20, wherein disposing the spring element adjacent the target tissue comprises disposing the first elongate flexible radiopaque filament to continuously follow a contour of a wall of the void or the surgical cavity.

23. The method of claim 18, further comprising contacting a hydrogel disposed on the first elongate flexible radiopaque filament with the target tissue.

24. The method of claim 18, further comprising limiting movement of the first elongate filament in tissue with an anchor, a hydrogel or a coating disposed on the first elongate radiopaque filament.

25. The method of claim 24, wherein the anchor comprises an echogenic clip, the method further comprising observing the clip with ultrasound.

26. The method of claim 18, further comprising causing biodegradation of the first elongate radiopaque filament.

27. The method of claim 18, wherein disposing the spring element adjacent the target tissue comprises threading the first elongate radiopaque filament into tissue, or clipping the first elongate radiopaque filament to tissue.

28. The method of claim 18, wherein the spring element further comprises a second elongate radiopaque filament.

29. The method of claim 28, wherein the first elongate radiopaque filament has a first radiopaque pattern and the second elongate radiopaque filament has a second radiopaque pattern different than the first radiopaque pattern, the method further comprising observing the first and second elongate radiopaque filaments under radiography and distinguishing the first and second elongate radiopaque filaments based on the first and second radiopaque patterns.

30. The method of claim 18, wherein the first elongate flexible radiopaque filament has two ends knotted together to form the closed loop.

31. The method of claim 18, wherein the spring element is free of material disposed inside the perimeter of the closed loop.

* * * * *

UNITED STATES PATENT AND TRADEMARK OFFICE
CERTIFICATE OF CORRECTION

| | | |
|---|---|---|
| PATENT NO. | : 12,109,432 B2 | Page 1 of 1 |
| APPLICATION NO. | : 18/355984 | |
| DATED | : October 8, 2024 | |
| INVENTOR(S) | : Vayser et al. | |

It is certified that error appears in the above-identified patent and that said Letters Patent is hereby corrected as shown below:

On the Title Page

Item (57), in "Abstract", in Column 2, Line 8, delete "maker." and insert --marker.-- therefor On page 3, in Column 1, under item (56) "Other Publications", Line 5, delete "saurgical" and insert --surgical-- therefor In the Specification In Column 5, Line 33, delete "SiO2," and insert --$SiO_2$,-- therefor In Column 10, Line 26, delete "discontinous" and insert --discontinuous-- therefor In Column 11, Line 25, delete "discontinous." and insert --discontinuous.-- therefor In Column 13, Line 61, delete "maker" and insert --marker-- therefor In Column 19, Line 12, delete "in in" and insert --in-- therefor In the Claims In Column 23, Line 11, in Claim 18, delete "cavity:" and insert --cavity;-- therefor In Column 23, Line 26, in Claim 20, after "to", delete "fill"

Signed and Sealed this
Thirty-first Day of December, 2024

Derrick Brent
*Acting Director of the United States Patent and Trademark Office*